(12) United States Patent
Mueller et al.

(10) Patent No.: US 6,171,251 B1
(45) Date of Patent: Jan. 9, 2001

(54) METHOD AND APPARATUS FOR OPTIMIZING DIRECT VESSEL IMPLANTS FOR MYOCARDIAL REVASCULARIZATION

(75) Inventors: Richard L. Mueller, Byron; Michael J. Rosinko, San Jose, both of CA (US)

(73) Assignee: Eclipse Surgical Technologies, Inc., Sunnyvale, CA (US)

( * ) Notice: Under 35 U.S.C. 154(b), the term of this patent shall be extended for 0 days.

(21) Appl. No.: 09/115,458

(22) Filed: Jul. 14, 1998

(51) Int. Cl.[7] ..................................................... A61B 5/02
(52) U.S. Cl. .............................. 600/481; 604/114; 606/15
(58) Field of Search ..................................... 600/300, 310, 600/481, 500, 508, 504; 604/114, 53; 606/15, 19, 7, 12, 36; 823/159

(56) References Cited

U.S. PATENT DOCUMENTS

| | | | |
|---|---|---|---|
| 4,576,145 | * 3/1986 | Tsuno et al. | 128/6 |
| 5,104,392 | * 4/1992 | Kittrell et al. | 606/15 |
| 5,125,926 | 6/1992 | Rudko et al. | 606/19 |
| 5,380,316 | 1/1995 | Aita et al. | 606/7 |
| 5,683,366 | 11/1997 | Eggers et al. | 604/114 |
| 5,703,985 | 12/1997 | Owyang | 385/117 |
| 5,713,894 | 2/1998 | Murphy-Chutorian et al. | 606/15 |
| 5,738,680 | 4/1998 | Mueller et al. | 606/15 |
| 5,766,164 | 6/1998 | Mueller et al. | 606/15 |
| 5,910,150 | * 6/1999 | Saadat | 606/159 |
| 5,976,164 | 11/1999 | Bencini et al. | 606/170 |

FOREIGN PATENT DOCUMENTS

0189329 * 1/1986 (EP) ........................................ 606/15

OTHER PUBLICATIONS

Mirhoseini, M., M.D., M. Muckerheide, and M.M. Cayton, RN. "Transventricular Revascularization by Laser." *Lasers in Surgery and Medicine.* 2:187–198 (1982).

Vineberg, Arthur, M.D.C.M., Ph.D., F.R.C.S. (Canada). "Revascularization via Healthy Myocardiall arteriolar Networks Compared with that Through Diseased Surface Coronary Arteries." *Israel Journal of Medical Science.* vol. II, No. 2–3, pp. 250–263.

Vineberg, Arthur, M.D., F.A.C.S. "Clinical and Experimental Studies in the Treatment of Coronary Artery Insufficiency by Internal Mammary Artery Implant." *The Journal of the International College of Surgeons.*

* cited by examiner

*Primary Examiner*—Cary O'Connor
*Assistant Examiner*—Michael Astorino
(74) *Attorney, Agent, or Firm*—Janet Castaneda; Ilene Janofsky

(57) ABSTRACT

Computer controlled apparatus and method for enhancing myocardial revascularization using direct vessel implants includes a probe for insertion into a proposed graft site to determine the condition of the site using criteria such as oxygen levels, contractility and pressure/flow rate differentials in conjunction with the parameters of the selected vessel graft. Transmyocardial revascularization procedures are performed to increase flow rates when needed and to supplement graft treatment where desired. A coring device creates the opening for the graft and correlates the size of the opening with contractility conditions and vessel conditions. Reinforcement sleeves may be placed around grafts, particularly vein grafts, to avoid excess compression of the graft. Graft site preparation and TMR treatment enhance angiogenesis and collateralization of the implant, and angiogenic drugs may be used to increase such effects.

35 Claims, 4 Drawing Sheets

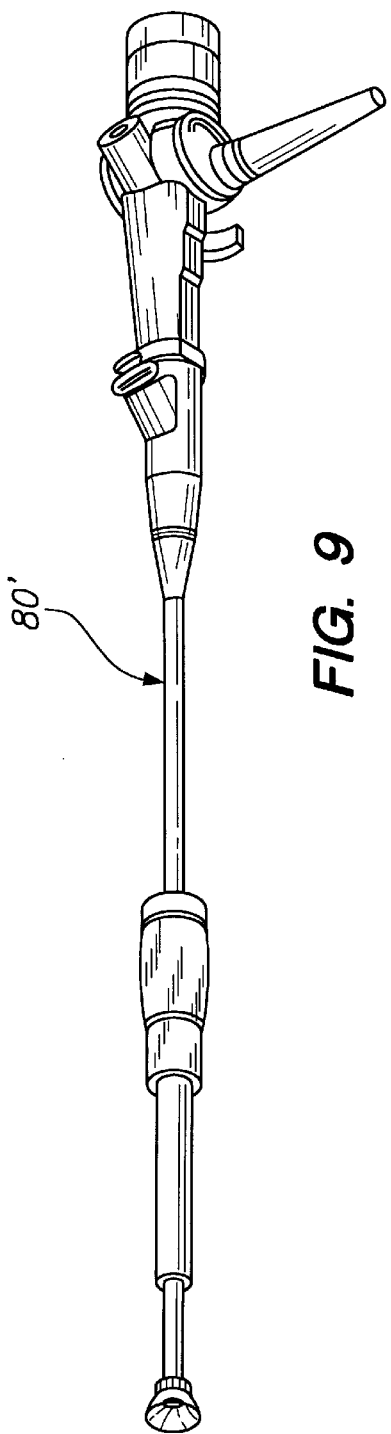
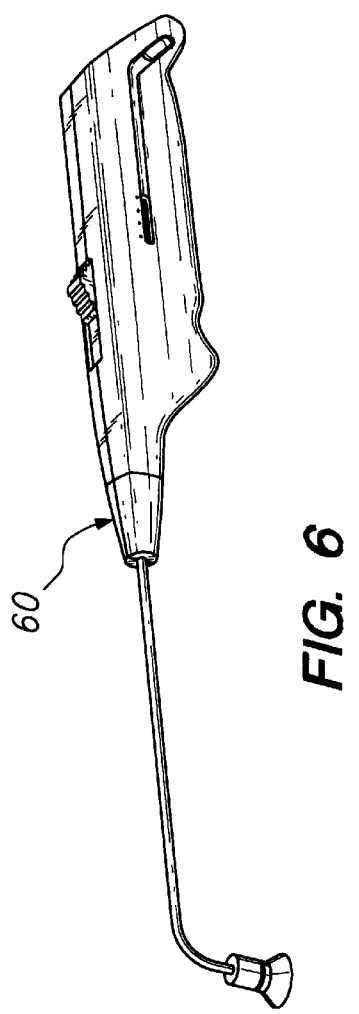
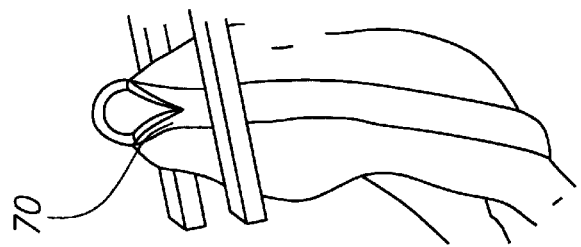

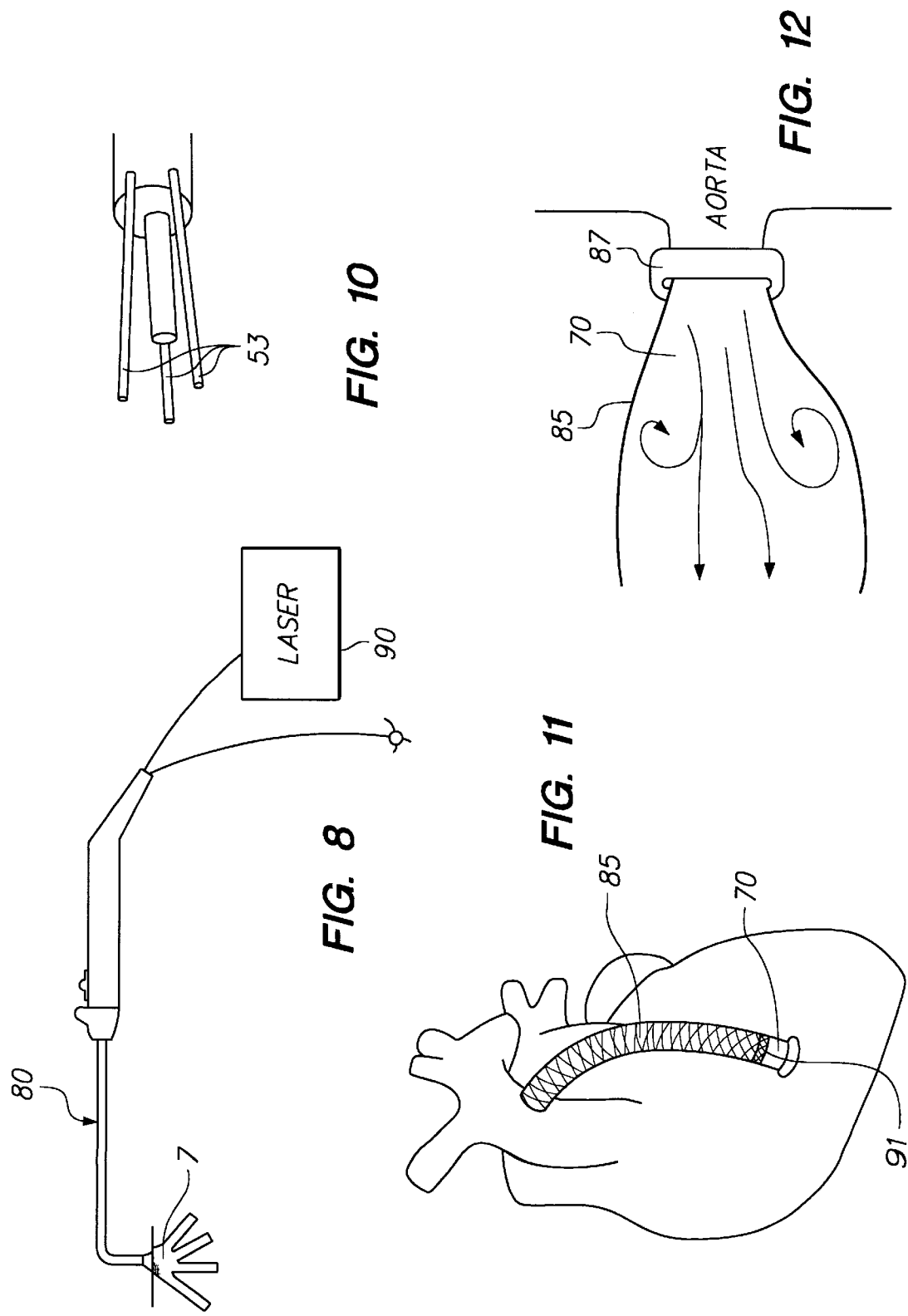

METHOD AND APPARATUS FOR OPTIMIZING DIRECT VESSEL IMPLANTS FOR MYOCARDIAL REVASCULARIZATION

FIELD OF THE INVENTION

This invention relates to the field of treatments for revascularizing heart tissue, and more particularly to methods and apparatus for selecting and preparing sites for implanting direct vessel grafts into the heart to maximize myocardial revascularization.

BACKGROUND OF THE INVENTION

Heart disease is a significant health problem which has been the subject of substantial medical study. Early treatments for angina pectoris, pain in the chest due to ischemia of the heart muscle, included, among others, attempts to revascularize the heart muscle by directly implanting vessels in the myocardium, by implanting tubes or vessels extending between the ventricle and the myocardium, and by performing acupuncture or channeling with a needle to carry blood from the ventricle into the myocardium. Acupuncture and channeling studies performed by P. K. Sen and P. Walter showed that the formed blood flow passageways and channels closed within a short period of time.

The Vineberg procedure, developed by Dr. Arthur Vineberg between 1930 and 1950, implanted the mammary artery into a tunnel created in an ischemic area of the myocardium of the left ventricle. Although the Vineberg procedure demonstrated successful animal trials which were supported by arteriograms from human subjects during the 1960's, the procedure remained controversial. Results of a 1972 randomized study conducted by the Veteran's Administration Hospital showed that just over 50% of the Vineberg grafts remained patent after one year. Dr. Vineberg reported higher patency rates in the results of a 20 year study in "Israel Journal of Medical Science", Vol. 11, No. 2–3, 1975, pgs. 250–263, which stated that implant patency was 80%, operative mortality was 2%, and anginal pain improved in 85% of cases. In the referenced article, Dr. Vineberg described the following surgical technique as necessary to achieve long term patency and collateralization with coronary arteries: careful preparation of the mammary artery with tying of the distal end and all but one or two of the intercostals; using forceps instead of a knife to tunnel at least 4 to 5 cm into an ischemic area of the myocardium located between branches of surface vessels in the apical, anterolateral or posterior arteriolar zones; and removal of the epicardium at the tunnel entrance.

The above treatments and associated research into Vineberg grafts and acupuncture techniques generally fell out of favor with the advent of coronary artery bypass grafts (CABG) which are vessel grafts attached proximally and distally around blockage sites in coronary arteries to "bypass" such blockages. Additionally, in the 1970's percutaneous transluminal coronary angioplasty (PTCA) procedures were introduced. Bypass surgery and PTCA have become commonplace; yet such procedures may not be able to revascularized all of the heart muscle, particularly the left ventricle of the heart, where blockages extend into the narrow distal portions of the coronary arteries.

Recent advances in cardiology have lead to improved bypass techniques and PTCA techniques (use of stents and atherectomy devices) thereby making it possible to attempt treatment of patients with severe coronary artery disease resulting in severely weakened, compromised hearts. Current statistics suggest that such patients present with less opportunity to achieve good CABG graft sites thereby resulting in estimates that 20–40% of CABG patents are not "fully" revascularized following CABG.

As the traditional treatments discussed above are expanded in use to attempt to assist severely weakened hearts, severely ischemic heart tissue is being treated and subjected to a sudden increase in blood flow. The flow/pressure differential which normally exists in the circulatory network supplying the heart muscle results from flow passing through vessels which progressively decrease in size as follows: the aorta, the coronary arteries, the arterioles, the capillaries, the veins, the coronary sinus, and finally into the heart chambers. Within this system, blood flows back and forth between capillaries and the myocardial sinusoids which receive blood from a constant exchange between sinusoidal vessels and the arterioles. In severely damaged heart tissue, this natural pressure differential is disrupted and may be unsuitable to accommodate the sudden introduction of relatively high pressure flow provided by a graft.

One alternative technique for treating areas untreatable with conventional CABG and PTCA procedures is known as transmyocardial revascularization (TMR). Procedures such as TMR, and drug therapy, enable treatment in areas that cannot be revascularized by CABG and PTCA. Although this technique was considered as early as the work of Dr. C. Beck "the Development of a New Blood Supply to the Heart By Operation", *Annals of Surgery*, Vol. 102, No. 5 (11/35) pp. 801–813, the method was not extensively studied until the work of Dr. M. Mirhoseini and M. Cayton, an example of which is found in "Lasers in Cardiothoracic Surgery in *Lasers in General Surgery* (Williams and Williams; 1989) pp. 216–223.

Clinical tests have demonstrated that TMR channels, which generally communicate with the ventricle, facilitate revascularization of the heart muscle and recovery of heart function. Recent studies further demonstrate that beneficial revascularization also occurs following creation of channels that do not remain patent and channels that do not communicate with the ventricular chamber. One mechanism for TMR revascularization is believed to be angiogenesis in response to injury created by the channel making device. Histology studies show the development of new vessels in the area of TMR channels. Dr. Vineberg reported in the article referenced above that new branches of implanted vessels occurred after a Vineberg procedure, and these branches joined with surrounding arterioles to revascularize the heart. Dr. Vineberg stated the collateralization to be caused by removal of the epicardium and lateral thrust because of the tied off distal end of the mammary artery. Angiogenesis research also is ongoing using agents such as growth factors and gene therapy products.

A laser device to perform TMR is described in Aita et al., U.S. Pat. No. 5,380,316, issued Jan. 10, 1995. In the procedure described in that patent, a number of channels are formed through the epicardium by means of a laser apparatus to extend through the myocardium to communicate with the ventricle. Other laser patents describing surgical transmyocardial revascularization include commonly owned U.S. Pat. Nos. 5,713,894; 5,738,680; 5,703,985; and 5,766, 164.

A need exists for combined modalities of treatment to enhance revascularization treatments while taking into consideration the condition of the myocardium to be treated.

A need exists for apparatus and methods to evaluate the condition of heart muscle, particularly the blood flow in potential treatment sites, to optimize treatment results by, when necessary, altering existing pressure/flow conditions to accept direct vessel implants into myocardium.

A need exists for cardiac treatment procedures which include diagnostic tools to evaluate and select treatment sites and tools to enhance treatment success by preparing compromised tissue to accept and benefit from the sudden introduction of a new blood supply utilizing, where appropriate, combined treatment modalities such as direct vessel implants and TMR.

A need exists for apparatus and methods to modify a vessel to be implanted within myocardium to enable the vessel, particularly a vein, to resist the contraction forces of the heart to prevent occlusion of the implant.

SUMMARY OF THE INVENTION WITH ADVANTAGES

Broadly, an advantage of the present invention is to provide apparatus and method to increase revascularization effects of direct vessel myocardial implants.

More specifically, an advantage of the present invention is to provide apparatus and method for selecting appropriate sites for direct vessel myocardial implants for myocardial revascularization.

It is a further advantage of the present invention to provide apparatus and methods for measuring blood flow rates and/or oxygenation conditions in myocardium to select sites for direct vessel myocardial implants for myocardial revascularization.

Yet another advantage of the present invention is to provide apparatus for enhancing blood flow rates in myocardium to correlate with blood flow rates in vessel grafts by increasing flow through rates at direct implant sites to provide continuous flow from the graft vessel through the implant site thereby maintaining graft patency and performance.

Still one more advantage of the present invention is to provide reinforcement sleeves for venous vessels to be implanted within myocardium for revascularization thereof.

Yet one more advantage of the present invention is to provide apparatus for measuring the contractile forces of the heart in the proposed area of a vessel implant to enable site and vessel graft preparation to compensate for such contractile forces.

An additional advantage of the present invention is to provide computerized control of a system for assessing direct vessel graft implant sites in myocardium and optimizing such sites and grafts using a combination of treatment modalities to achieve myocardial revascularization.

The present invention is a computerized vessel graft implant site selection and preparation system for revascularizing ischemic heart tissue by improving the results of direct vessel grafts into the heart muscle to achieve myocardial revascularization in ischemic tissue.

The system evaluates heart tissue by providing a sensor to measure at least one parameter describing the condition of tissue at a proposed implant site. In a preferred embodiment, the parameter measured is blood flow rate at select vessel graft sites. The system includes tools to increase blood flow rates, when necessary, and further measures vessel graft parameters so that any alterations in myocardial flow rates are correlated with vessel characteristics.

In another aspect of the invention, the system may employ additional sensors to determine additional tissue parameters, such as contractility of the affected heart muscle to ensure that flow rates are determined when the heart muscle is not contracting. Contractility information also can be used to select a graft reinforcement sleeve which is strong enough to resist contractile forces, yet flexible. Tissue oxygenation sensor results may be inputs to the computerized control system to validate muscle viability.

The procedure for using the system attaches a probe to myocardium to measure the selected parameter at a proposed graft site. A sensor operatively connected to the probe provides readings, such as flow rates, to the computer system. If the flow rate is sufficient to allow adequate flow from the proposed graft, a tool is used to create an opening in the proposed site and the vessel graft is inserted and secured within the opening.

If the flow rate is insufficient, transmyocardial revascularization (TMR) channels and pathways may be formed until the flow rate is increased to support run off from the graft. Optional sensors determine contractility forces of the heart at the proposed site, and reinforcement sleeves may be placed around the vessel graft prior to implantation to assist the graft in resisting the contractile forces of the heart. Angiogenic drugs may be used to enhance treatment.

These and other objects, advantages and features of the present invention will be apparent to those skilled in the art from the following detailed description and the accompanying drawings.

BRIEF DESCRIPTION OF THE DRAWINGS

FIG. 6 is a side plan view of a coring device for preparation of the implant site.

FIG. 7 is a view of a vessel undergoing preparation for implant into myocardium.

FIG. 8 is a side plan view of a TMR device for enhancing flow rates at a selected implant site and for supplemental TMR treatment.

FIG. 9 is an elevated plan view of a MIS TMR device for use in MIS implant procedures.

FIG. 10 is a side plan view of the distal end of a TMR device having multiple fibers.

FIG. 11 is a plan view of a reinforcement sleeve mounted around a vein implant.

FIG. 12 is a side plan view of a flow restrictor device.

DETAILED DESCRIPTION OF PREFERRED EMBODIMENTS

The present invention is a computerized vessel graft implant site selection and preparation system for revascularizing ischemic heart tissue by improving patency and performance of direct vessel grafts into the heart muscle to achieve myocardial revascularization in ischemic tissue.

The system evaluates heart tissue by measuring blood flow rates to select vessel implant sites. The system includes tools to increase blood flow rates, when necessary, at selected sites, and further measures flow rates in the vessel to be implanted so that alterations in myocardial flow rates are performed to result in a correlation between the selected vessel and myocardium flow rates.

The system further enables the use of venous as well as arterial vessels for grafts by providing reinforcement sleeves for vein grafts to compensate for contractile heart forces.

The procedure for using the system places a flow sensor probe within myocardium to measure the flow rate at a proposed graft site. A sensor operatively connected to the probe provides pressure readings to the computer system. If the flow rate is sufficient to allow adequate flow from the proposed graft, a tool is used to create an opening in the proposed site and the vessel graft is inserted and secured within the opening. If the flow rate is insufficient, TMR channels and pathways may be formed in the proposed site until the flow rate is increased to support run off from the graft. Optional sensors may be used to determine contractility forces of the heart at the proposed site, and reinforcement sleeves may be placed around the vessel graft prior to implantation to assist the graft in resisting the contractile forces of the heart. Tissue oxygenation also may be measured using sensors.

Figure 1:
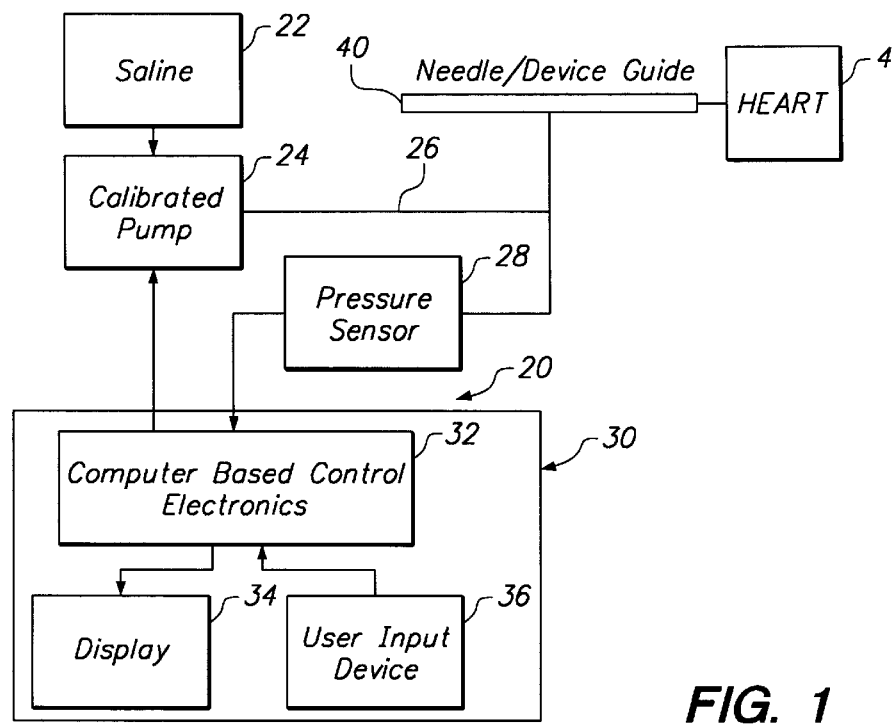
FIG. 1 is a block diagram of apparatus and the control system for selecting sites for direct vessel implants in heart tissue for the purpose of revascularization.

While a variety of embodiments of the present invention are disclosed herein, one exemplary presently preferred embodiment demonstrating control of the computerized vessel graft implant site selection system is illustrated generally as reference number 20 in FIG. 1. The block diagram in FIG. 1 shows the mechanism for estimating the potential blood flow rate at a potential direct vessel implant site. A fluid reservoir 22 filled with saline or Ringer's solution or the like is connected to a pumping device 24 which conveys saline from the reservoir 22 along fluid path 26 and through a probe 40 for connection to a proposed graft site in the heart 4 of a patient. The pumping device may be a syringe pump driven by a stepper motor, a peristaltic pump, or a diaphragm pump with a weight scale or flow meter to allow calibrated flow from the reservoir 22. An example of a suitable pump is a Cole Parmer Syringe Infusion Pump.

A pressure sensor 28 is connected to the fluid path 26, or it may be attached directly to the distal end of probe 40. The pressure sensor 28 is connected to the computer system 30 which monitors the pressure and controls the pumping rate.

The computer system 30 may include a custom microprocessor control circuit. Alternatively, a conventional computer having a data acquisition card capable of reading and converting analog voltages from the pressure sensor may be used. In this system, a serial connection port of the computer is suitable for attachment and control of the pumping device 24. The system illustrated in FIG. 1 is a conventional computer microprocessor 32 fitted with a Keithly Metrabyte DASCard 1000 data acquisition card. The computer system 30 further includes a display screen 34 and a user input device 36.

Figure 2:
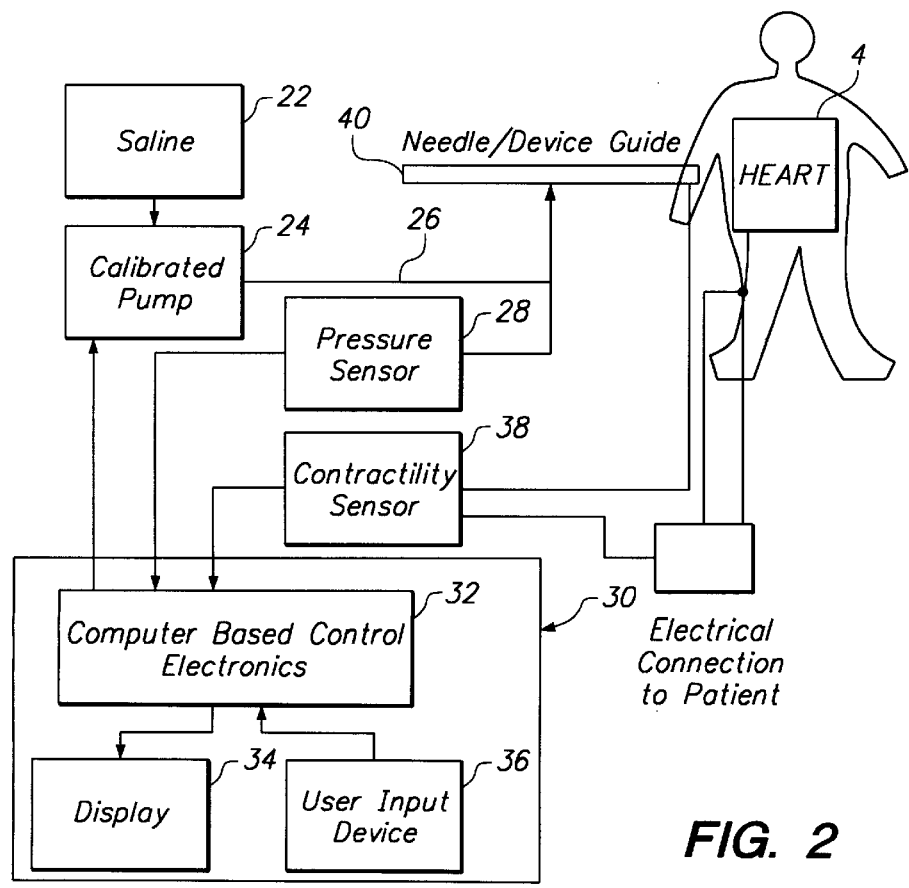
FIG. 2 is a block diagram of an alternative aspect of apparatus and the control system for selecting sites for direct vessel implants in heart tissue for the purpose of revascularization.

An alternative computerized vessel graft implant site selection system, with like components bearing the same reference numbers, is shown in FIG. 2. The system of FIG. 2 has at least one additional sensor 38 for determining contractility of the heart muscle. The sensor 38 may be a conventional ECG device, such as ECG machines generally in use as monitors in operating room. In this aspect of the invention, the sensor 38 detects the QRS heart wave complex and provides confirmation of contraction of the heart to the computer system 30. The computer system 30 enables measurement of pressure by the pressure sensor 28 only after the QRS signal when the heart is not contracting. Alternatively, the sensor 28 may be a bipolar electrode connected to the distal tip of the probe 40 and further connected to the patient as shown. The connection to the patient may be accomplished by connecting the bipolar electrode to the conventional ECG device.

If the contractility sensor 38 is not present as in FIG. 1, the FIG. 1 system can correlate measurement of pressure during the resting phase of the heart cycle by monitoring the pressure with a fixed zero flow rate. The resulting pressure profile demonstrates increased pressure during contraction of the heart. Filtering or gating may be used to eliminate contractility input.

Figure 3:
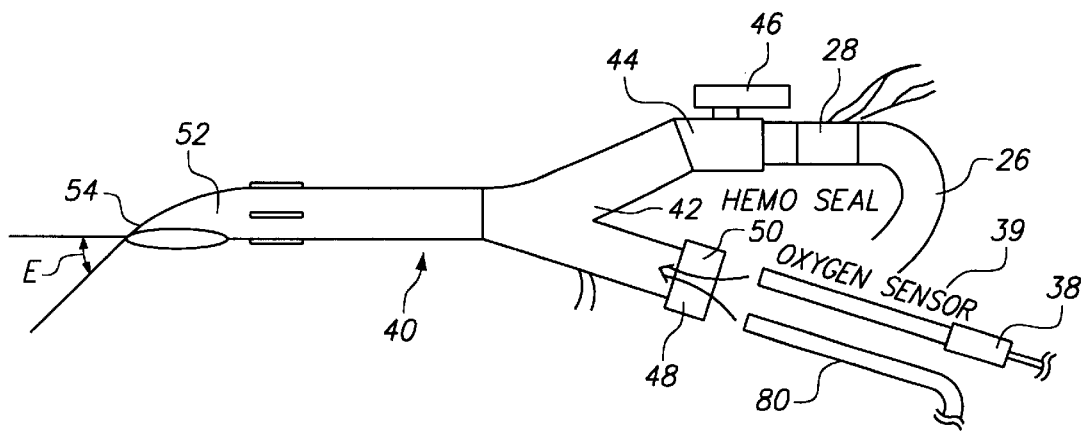
FIG. 3 is a side plan view of a probe for measuring tissue conditions, such as flow rates and oxygenation, at proposed implant sites.
Figure 4:
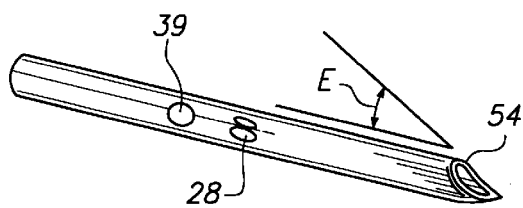
FIG. 4 is a detail view of the distal end of the probe showing the insertion end and one or more sensors.

FIGS. 3 and 4 illustrate the probe 40 for insertion into proposed vessel graft sites within myocardium. The probe 40 is a handpiece having a proximal end 42 defining a fluid input port 44 controlled by valve 46. As discussed above, the probe 40 may include the pressure sensor 28 which, in this case, is a thin film or dome pressure sensor shown connected to the fluid line 26. Probe 40 further includes a port 48 with a blood seal 50 for attachment of an oxygen sensor 39 or the contractility sensor 38 shown in the FIG. 2 embodiment. The oxygen sensor provides information regarding the relative health of the proposed graft site thereby adding valuable input to site selection criteria.

The distal end 52 of the probe 40 includes a sharpened needle point 54 for insertion of the probe into myocardial tissue. As best shown in FIG. 4, the oxygen sensor 39 and pressure sensor 28 may be mounted on the insertion point of the probe 40. Alternatively, a separate needle may be advanced and retracted into the generally hollow tube for insertion into tissue to secure the probe 40 to the heart. The distal end 52, or the distal end of an internal needle, may be angled to allow the probe to be rotated to access other portions of myocardium from a single entry point. The radius at the end of the needle allows the probe to be rotated to allow angled tissue access, show as E, by the probe.

The needle used to deliver fluid to the tissue for flow rate determinations should be calibrated prior to use, although calibration may be performed by the manufacturer with confirmation by the user with a simple calibration confirmation command to the computer system 30. Calibration may be performed manually prior to insertion of the probe 40 into tissue by an input to the computer input device 36 to initiate pumping by the pumping device 24 to deliver fluid at a fixed flow rate during pressure measurement. The procedure is repeated at several flow/pressure points to allow calibration of the resistance to flow through the needle.

The computerized vessel graft implant site selection and preparation system is used as follows after calibration, if necessary, as discussed above. The distal tip 52 of the probe 40 is inserted into myocardium at a proposed direct graft site. Oxygen content is measured if the optional oxygen sensor 39 is present. Upon confirmation of sufficient tissue oxygen from the sensor 39, a command is given to the computer system 30 using the user input device 36 to perform a flow estimation and valve 46 is opened. The computer system 30 controls the pumping device 24 to increase flow of fluid through the pump during pressure monitoring. As flow increases, pressure increases because of resistance from the needle and from the flow conditions within the target myocardium.

Figure 5:
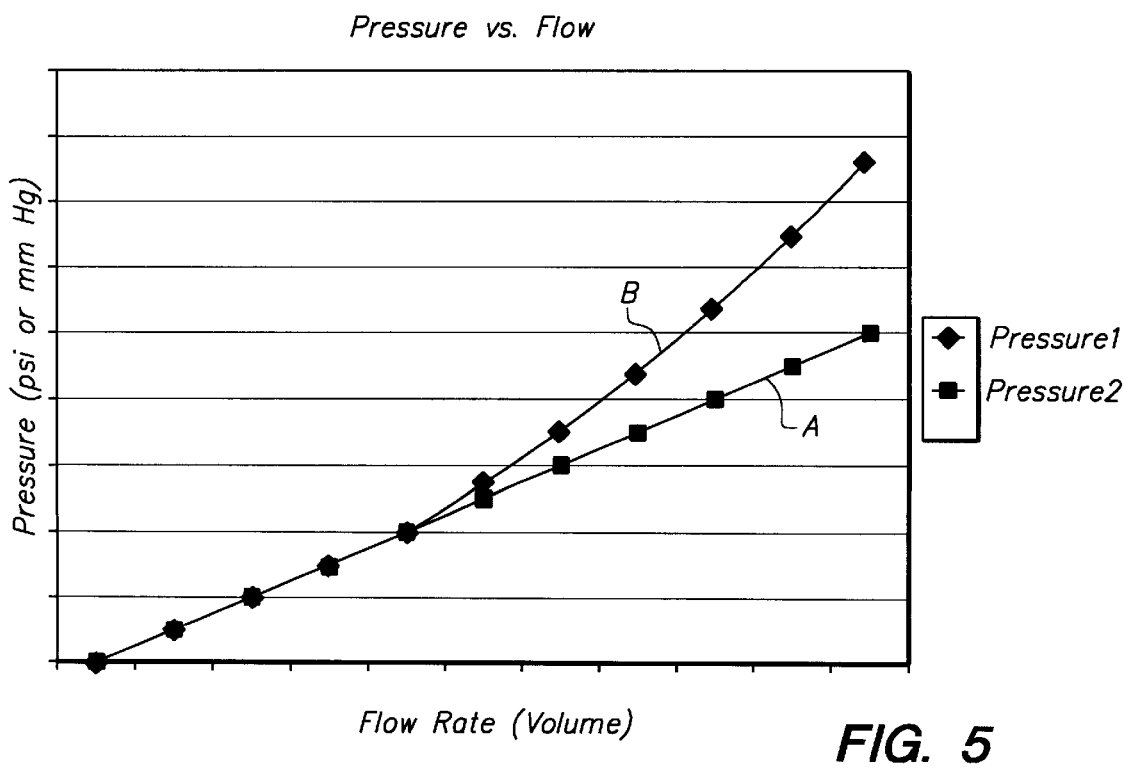
FIG. 5 is a graph showing pressure versus flow rates.

FIG. 5 is a graphical representation of pressure vs. flow rate. Curve Pressure I, "A", represents an unrestricted pressure/flow curve when the probe is not inserted in myocardium and flow is inhibited only by the resistance of the system components, thereby representing the calibration curve. Curve Pressure 2, "B", represents the pressure/flow rate of the myocardium when the probe is inserted in the tissue. In curve "B", the pressure increases above the calibration curve "A" when flow from the reservoir 22 exceeds the blood flow rate in the myocardium. The flow rate of the myocardium thus is estimated to be the flow rate at which the pressure exceeds the calibrated rate. Measurements generally are stated as volume per unit of time(ml/min)/psi or mmHg. The estimated flow rate is displayed on the display device 34.

The displayed flow rate is compared with the flow rates measured in studies of successful long term, patent grafts, which is estimated optimally to be approximately 25 to 75 ml/minute. Long term patency will require a minimal continuous flow through the site to maintain graft patency. In addition, the available graft flow rate is measured as a second test of compatibility. Preferred implant connections will have a minimal run-off rate in myocardium and a graft supply flow rate sufficient to provide required flow without excessive turbulence or localized fluid stagnation. If the rates are found compatible, the vessel graft can proceed.

FIG. 6 shows a system component for forming a pathway into the selected myocardial site for insertion of the vessel graft. A mechanical coring device 60, such as the device described in U.S. Pat. Nos. commonly owned U.S. Pat. Appln. Ser. No. 08/908,816, filed on Aug. 8, 1997, now U.S. Pat. No. 5,976,164 hereby incorporated by reference, may be used to create the opening for the graft, or to create additional run-off channels. Device 60 is a motorized, rotating coring device for removing a core of tissue. Any coring device may be used, and energy delivery devices also may be employed to prepare the graft site. Such devices include those found in U.S. Pat. Nos. 5,713,894; 5,738,680; 5,703, 985; 5,766,164; 5,125,926; 5,683,366; and 5,380,316 which are hereby incorporated by reference herein. The amount of coring and the diameter of the opening preferable is correlated with the type of graft to be used (vein as opposed to artery) and the contractile forces at the site to avoid excessive compression of the implanted graft. This is particularly important for vein grafts. The computer system 30 may be programmed to calculate the diameter of the opening after determining t size of the implant and the contractility of the site.

As shown in FIG. 7, the vessel, such as the LIMA 70, is detached from the chest wall and freed for insertion into the opening created by the coring device 60. Particularly for vein implants, contractility readings are used to calculate implant opening size to avoid excessive compression on the implant. Additionally, as shown in FIG. 11, reinforcement sleeves 85 or stents made from dacron, teflon, other plastic materials and biocompatible metals may be placed around the vein prior to implanting the graft into the opening. The distal ends of the sleeves 85 preferably are configured with sewing or stapling eyelets 91 for ease of attachment. The vessel may be pretested using a pressure cuff to determine the degree of support needed. Preferably, the vessel flow rate is similar to the measured or modified run-off rate to maintain flow and a balance between blood supply and demand.

FIG. 12 illustrates a method for restricting flow in the vessel graft when a balance between blood supply and demand is not achieved by modification of the implant site. An orifice restrictor 87 at the distal end of the graft 70, or the sleeve 85, may be used to reduce flow through the implant 70.

Using the system shown in FIG. 2, the contractility results also may be used to correct the pressure curve "B" for heart contraction events. Inputs from the sensor 38 enable the computer system 30 to generate a pressure/flow curve "B" which includes readings taken only when the heart is not contracting, as described above.

In those cases where a preferred graft implant site does not have a flow rate sufficient to support the graft, and other sites are not available, TMR or other revascularization procedures may be performed at and around the preferred site to increase the flow rate and enhance collateralization and other angiogenesis. Such a procedure may be performed with any TMR system utilizing mechanical devices or energy sources such as lasers, RF, ultrasound, microwave, heat and fluid jets. Suitable laser devices 80 and 80' are shown in FIGS. 8 and 9 which are described in U.S Pat. Nos. 5,713,894; 5,738,680; and in commonly owned U.S. Pat. Appln. Ser. No. 08/794,733; now U.S. Pat. No. 6,027,497 and other suitable laser devices may be found in U.S. Pat. Nos. 5,703,985; 5,766,164; 5,125,926; 5,683,366, all of which are hereby incorporated by reference. The TMR tool shown in FIG. 9 is particularly suitable for MIS procedures when direct vessels implantation is performed in an MIS setting.

As shown in FIG. 3, a TMR device also may be inserted through port 48 and through curved distal tip 54 to allow TMR channels to be made at more than one angle from a single entry point into the myocardium, or the TMR device may be configured with a curved needle as in FIG. 4 to provide angled channels 7 as shown in FIG. 8. Such channels may include stimulation zones as described in U.S. Pat. Appln. Ser. No. 08/664,956 and may or may not extend into the ventricle. When inserted through probe 40, blood seal 50 prevents blood loss through port 48, and the laser delivery device may be retracted to a resting position within arm 48 when not in use. Laser TMR devices are connected to excimer, CO2, holmium or other suitable lasers, such as the holmium laser 90 shown in FIG. 8. As an alternative to the curved distal tip 54, the distal end of the laser 80 also may be configured as shown in FIG. 10. In this embodiment, the distal end of the laser includes a plurality of laser fibers 53 for simultaneously creating a plurality of channels within the target tissue.

Following creation of channels to assist flow within and around the graft site, flow measurements are repeated to confirm that flow conditions are optimized to achieve desired constant flow run off from the graft. While the frequency of graft occlusion with flow rates exceeding 50 ml/min. is reported to be very low, implants using the proposed treatment modalities suggested above may allow flow rates significantly lower. The TMR treatment device also may be used to supplement treatment by performing TMR in other ischemic areas of the myocardium.

Angiogenic drugs may be added to the implant sites to enhance revascularization. Such drugs include VEGF, other growth factors and gene therapy agents.

It will be recognized by those skilled in the art that conventional wall motion studies may be used to indicate the general contractility of the heart tissue if desired, although site specific information provided by the sensors may be more accurate. Additionally, thallium scans and the like may be performed to indicate flow rates generally.

The foregoing description of a preferred embodiments of the invention has been presented for purposes of illustration and description. It is not intended to be exhaustive or to limit the invention to the precise forms disclosed. Obviously, many modifications and variations will be apparent to practitioners skilled in this art. The scope of the present invention is therefore limited only by the scope of the claims appended hereto.

What is claimed is:

1. An apparatus for use in a procedure to revascularize a heart by implanting a vessel into myocardium comprising:
   a pressure transducer adapted for connection to heart tissue, said transducer measuring a fluid flow rate for selecting an implant site;
   a microprocessor for receiving and processing input from said pressure transducer; and
   a tool for creating an injury in heart tissue at least at the selected implant site.

2. The apparatus of claim 1 further comprising a probe for insertion into myocardium at said site, the probe connected to the pressure transducer.

3. The apparatus of claim 2 further comprising a fluid source connected to the probe and to the microprocessor, the microprocessor controlling flow from the fluid source to the probe for delivery to the myocardium at the site.

4. The apparatus of claim 2 further comprising a sensor for measuring tissue contractility operatively connected to the probe.

5. The apparatus of claim 4 further comprising a sensor for measuring oxygen content of tissue operatively connected to the probe.

6. The apparatus of claim 2 further comprising a sensor for measuring oxygen content of tissue operatively connected to the probe.

7. The apparatus of claim 6 further comprising a sensor for measuring tissue contractility operatively connected to the probe.

8. The apparatus of claim 1 wherein said injury creating tool is a tool for creating an opening at the selected site for insertion of an implant.

9. The apparatus of claim 8 further comprising a transmyocardial revascularization device.

10. The apparatus of claim 9 wherein the tool for creating an opening at the selected site is a coring tool.

11. The apparatus of claim 1 wherein said injury creating tool is a coring tool.

12. The apparatus of claim 1 wherein the tool is a laser delivery device adapted for attachment to a laser energy source.

13. The apparatus of claim 1 wherein the tool is a laser energy delivery device adapted for attachment to a laser energy source, said laser energy delivery device both creating an opening at the selected site for insertion of implant and revascularizing heart tissue.

14. A method for selecting a site for placement of a vessel graft into myocardium of a heart for the purpose of revascularizing the heart, the method comprising the following acts: a) placing a sensor in contact with at least one possible graft site within the myocardium; b) measuring at least one localized tissue parameter at the at least one possible graft site to select an implant site; c) creating an opening in myocardium at the selected site; and d) implanting a direct vessel graft into the opening.

15. The method of claim 14 further comprising the act of creating at least one blood flow path within the at least one possible graft site if an acceptable tissue parameter is not found following act b).

16. The method of claim 14 further comprising the act of placing a reinforcing sleeve over the direct vessel graft prior to act d).

17. The method of claim 14 further comprising the act of using a transmyocardial revascularization tool to form revascularization channels at least around the selected site to enhance vessel patency and graft performance.

18. A system for selection and preparation of a proposed vessel implant site to revascularize heart tissue comprising:
   a guide for insertion into heart tissue in the area of a proposed vessel implant site;
   a fluid path coupled to said guide;
   a device to evaluate the condition of said site in contact with said fluid path;
   a monitoring device coupled to said evaluation device; and
   a tool to create an opening in heart tissue for a vessel implant in combination with said guide.

19. The system of claim 18 further comprising a fluid source for said fluid path coupled to a pumping device.

20. The system of claim 19 wherein said monitoring device is a microprocessor coupled to said pumping device.

21. The system of claim 18 wherein said tool is a mechanical tissue removal device.

22. The system of claim 18 wherein said tool is an energy delivery device adapted for connection to an energy source.

23. The system of claim 18 wherein said tool is also a revascularization device used to increase blood flow rates in heart tissue.

24. The system of claim 18 further comprising a revascularization device in combination with said guide.

25. The system of claim 18 further comprising a sensor for determining contractility of heart muscle coupled to said monitoring device.

26. A device for use in selection and preparation of a vessel implant site to revascularize heart tissue comprising:
   a hollow probe for insertion into heart tissue;
   a device to evaluate the condition of a site for a vessel implant attached to said probe; and
   an energy delivery device translatable within said probe for delivery of energy to heart tissue to create an opening for said vessel implant.

27. The device of claim 26 wherein a proximal end of said probe defines a first fluid input port controlled by a valve and said evaluation device is a pressure transducer.

28. The device of claim 27 further comprising one or more oxygen sensors and contractility sensors in combination with said probe at a second proximal port.

29. The device of claim 26 further comprising one or more pressure sensors and oxygen sensors mounted at the distal portion of said probe proximal to said distal end.

30. The device of claim 26 further comprising a sharp distal tip element in combination with said hollow probe to secure said probe to heart tissue.

31. The device of claim 30 further comprising one or more oxygen and contractility sensors attached to said sharp distal tip element.

32. The device of claim 26 wherein a distal end of said sharp element is angled to facilitate access to other portions of heart tissue from a single insertion point.

33. The device of claim 26 wherein said energy delivery device is also a revascularization device for revascularizing heart tissue.

34. An apparatus for use in a surgical procedure to revascularize a heart comprising: a body defining proximal and distal ends, the proximal end defining at least two arms having lumens therethrough, the lumen of at least one of the two arms for insertion of access tools and further having a blood seal, at least one of the two arms having a valve for closing off access to the lumen; the distal end having a piercing device suitable to pierce myocardium; and at least one sensor operatively attached to the body for determining a localized tissue condition.

35. A kit for use in a procedure to revascularize a heart by implanting a vessel into myocardium comprising:

a probe adapted for connection to a heart and to a microprocessor;

at least one sensor operatively connected to the probe for measuring at least one localized tissue condition, the sensor adapted for inputting results about the at least one localized tissue condition to a microprocessor;

a coring tool for creating an opening at a selected implant site for insertion of a vessel therein;

an injury creation device for creating injury in heart tissue around at least the selected site for enhancing revascularization effects of the vessel; and one or more reinforcement sleeves adapted to be placed around the vessel prior to implanting the vessel in the opening formed at the selected implant site.

* * * * *